United States Patent [19]

Gisi

[11] Patent Number: 4,927,823
[45] Date of Patent: May 22, 1990

[54] FUNGICIDES

[75] Inventor: Ulrich Gisi, Wenslingen, Switzerland

[73] Assignee: Sandoz Ltd., Basel, Switzerland

[21] Appl. No.: 278,054

[22] Filed: Nov. 30, 1988

[30] Foreign Application Priority Data

Dec. 2, 1987 [GB] United Kingdom ............... 8728236

[51] Int. Cl.$^5$ .................... A01N 37/12; A01N 43/08; A01N 43/76; A01N 43/84
[52] U.S. Cl. ................... 514/237.5; 514/376; 514/471; 514/472; 514/538; 514/539
[58] Field of Search ............ 514/237.5, 376, 471, 514/472, 538, 539

[56] References Cited

U.S. PATENT DOCUMENTS 4,585,763 4/1986 Devoise Lambert et al. ...... 514/376
4,753,934 6/1988 Nickl et al. ...................... 514/237.5

*Primary Examiner*—Allen J. Robinson
*Attorney, Agent, or Firm*—Gerald D. Sharkin; Richard E. Vila; Joanne M. Giesser

[57] ABSTRACT

The invention relates to synergistic mixtures comprising as active ingredients
(a) a compound of formula I

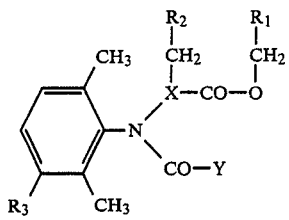

wherein
$R_1$ and $R_2$ are both H or together form a covalent bond,
$R_3$ is H, Cl or Br
X is CH or N and
Y is $CH_2OCH_3$, 2-furyl, benzyl or $CH_2Cl$ in association with
(b) the compound of formula II

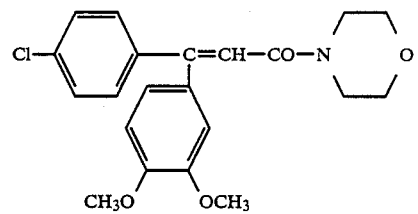

in a fungicidally effective aggregate amount, and the use of such mixtures.

8 Claims, No Drawings

FUNGICIDES

The present invention relates to fungicides, more particularly to oomycetes controlling fungicides.

Although a wide variety of oomycetes controlling fungicides are known, the need exists for still more effective fungicides.

It has now been found that the use of
(a) a compound of formula I

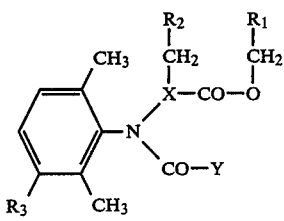

wherein
$R_1$ and $R_2$ are both H or together form a covalent bond,
$R_3$ is H, Cl or Br,
X is CH or N and
Y is $CH_2OCH_3$, 2-furyl, benzyl or $CH_2Cl$ in association with
(b) the compound of formula II

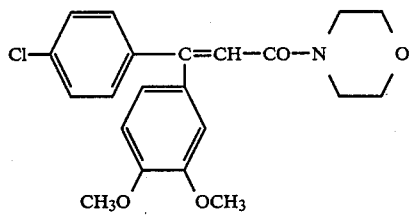

is particularly effective in combatting or preventing fungal diseases.

The invention accordingly provides a method of fungal diseases in plants which comprises applying to the plants, seeds or soil, in admixture or separately, a fungicidally effective aggregate amount of a compound of formula I and the compound of formula II.

Compounds of formula I, particularly suitable for use in the method of the invention are those wherein $R_1$, $R_2$, $R_3$, X and Y are
(i) H, H, H, CH and 2-furyl resp. (common name furalaxyl)
(ii) H, H, H, CH and $CH_2OCH_3$ resp. (common name metalaxyl)
(iii) H, H, H, CH and benzyl resp. (common name benalaxyl)
(iv) covalent bond ($R_1+R_2$), H, N and $CH_2OCH_3$ resp. (common name oxadixyl,
(v) covalent bond ($R_1+R_2$), H, CH and $CH_2Cl$ resp. (common name milfuram, ofurace)
(vi) covalent bond ($R_1+R_2$), Cl, N and $CH_2OCH_3$ resp. and
(vii) covalent bond ($R_1+R_2$), Br, N and $CH_2OCH_3$ resp.

The compounds of formula I are known fungicides; they have systemic fungicidal activity against i.a. Plasmopara spp and Phytophthora spp.

The compound of formula II is known under the common name dimethomorph. It is disclosed in the European Pat. Appln. 120321 and shows fungicidal activity with relatively low systemic activity against oomycetes such as Phytophthora spp.

The use of dimethomorph in combination with a compound of formula I, particularly with one of the compounds (i) to (vii) specifically mentioned above, more particularly with benalaxyl, metalaxyl or oxadixyl, most preferably with oxadixyl, surprisingly and substantially enhances the fungicidal effectiveness of the compounds of formula I, and vice versa. The method of the invention is particularly useful under circumstances where the development of phenylamide resistant oomycetes strains, especially field strains of Plasmopara spp and of Phytophthora spp is likely. The method of the invention decreases the risk of fungal subpopulation developing resistance against compounds of formula I and is surprisingly effective against Oomycetes strains which did already develop resistance against such compounds of formula I.

The method of the invention is in particular suitable for use against fungi of the class Oomycetes such as Phytophtora spp, Plasmopara spp, Peronospora spp, Pseudoperonospora spp, Sclerophthora spp, Bremia spp and Pythium spp in crops such as grapevines, tomato, hops, cacao, tobacco, potato, peas, onions, cucurbits, lettuce cultures or in eucalyptus, or turf.

Examples of fungus/crop systems against which the method of the invention is particularly indicated are *Pseudoperonospora cubensis* in cucurbits, *Plasmopara viticola* in grapevines and most particularly *Phytopthora infestans* in potatoes and tomatoes.

The compounds of formulae I and II may for example be applied in spray form, e.g. employing appropriate dilutions of a soluble concentrate or of a wettable powder formulation in water.

Suitable fungicidally effective aggregate amounts of the compounds of formulae I and II lie in the range of from 500 to 1000 g/ha of crop locus. In general, satisfactory results will be obtained when employing from 150 to 300 g/ha, e.g. 200 g/ha of a compound of formula I and from 350 to 700 g/ha, e.g. 500 g/ha of the compound of formula II.

The application rate may also be expressed in terms of concentrations. Spray liquors suitable for use in for example grapevines or potatoes comprise from 50 to 100 g per hectoliter. The spray treatment involves usually foliar application till the run-off. This corresponds in general with a spray volume of from 600 to 1000 liters per hectare of crop locus, depending i.a. on the growth stage of the crop.

Other pesticides e.g. fungicides, bactericides, insecticides, acaricides, herbicides or plant growth regulating agents may be used in addition to the compounds of formulae I and II to enhance the activity of the association of the invention or to widen its spectrum of activity; the addition of a contact fungicide may be particularly advantageous.

The term contact fungicide as used herein is intended to relate to fungicides having no or no significant systemic action and comprises by way of example copper fungicides, ethylene bis[dithiocarbamato]metal compounds such as mancozeb, maneb, zineb, propineb, trichloromethane-sulphenylphthalimides and analogues such as captan, captafol and folpet etc.

The weight ratio compound of formula I:compound of formula II will depend on various factors such as the mode of application, the disease to be combatted, the crop involved, the application time etc.

In general satisfactory results will be obtained when the weight ratio of compound of formula I:compound of formula II lies in the range of from 1:1 to 1:6.5, more preferably from 1:2 to 1:6.5 as illustrated by the experimental test results for the range of from 1:2.5 to 1:6.3.

The invention also provides fungicidal composition comprising a compound of formula I and the compound of formula II e.g. in a weight ratio within the range specified hereinabove.

Such compositions of the invention may be formulated in any conventional form, for example in the form of a twin packet, or of an emulsifiable concentrate, a soluble concentrate, a soluble concentrate, a wettable powder or water dispersible granule. Such compositions may be produced in conventional manner, for example by mixing a compound of formula I, e.g. oxadixyl with the compound of formula II with appropriate adjuvants such as diluents and optionally other formulating ingredients such as surfactants.

The term diluent as used herein means any liquid or solid agriculturally acceptable material—including carriers—which may be added to the active constituents to bring them in a suitable application or commercial form. It can for example be talc, kaolin, diatomaceous earth, mineral oil, or water.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty sulphate, an ethoxylated alkylphenol and an ethoxylated fatty alcohol.

In general, the formulations include from 0.01 to 90% by weight of active agent, from 0 to 20% agriculturally acceptable surfactant and 10 to 99.99% solid or liquid diluent, the active agent consisting of a compound of formula I and dimethomorph and optionally other active agents. The formulations may additionally contain additives such as pigments, thickeners and the like.

The invention is illustrated by the following examples, wherein parts and percentages are by weight.

TEST METHOD

Determination of fungicidal activity (EC 90) *Phytophthora infestans* on tomato

Young potted tomato plants (3–4 leaf stage) are sprayed with an aqueous spray liquid comprising 500, 125, 31, 8 and 2 ppm of a compound of formula I, the compound of formula II, or of a mixture of a compound of formula I with the compound of formula II in various weight ratios. The compounds of formula I and II are employed in aqueous solution of the wettable powder formulation specified in the Formulation Examples 1 and 2 hereinafter. The mixtures of the compounds of formula I and II are employed as tank mixtures thereof.

One day after the fungicide treatment the treated plants leaves are inoculated with a sporangium suspension ($10^5$ sporangia/ml) of *Phytophthora infestans*. The plants are then transferred to a tent providing 100% relative atmospheric humidity at an ambient temperature of 18° and a day length of 16 hours. Disease control is evaluated 4–5 days thereafter, by comparing the treated plants (leaves) with untreated, similarly inoculated plants (leaves).

The inoculation is performed by using either sensitive strains or strains which developed resistance against compounds of formula I.

The disease control is expressed for each test concentration as % control. This allows the determination of the EC 90 exp. value, i.e. the concentration of each compound or combination allowing 90% disease control.

The experimental results (EC 90 exp.) for a given weight ratio compound of formula I:compound of formula II is compared with the corresponding EC 90 theor. value, i.e. the concentration of that particular mixture allowing 90% disease control calculated according to Wadley.

$$EC(I + II)90\ theor. = \frac{a + b}{\frac{a}{EC(I)90\ exp.} + \frac{b}{EC(II)90\ exp.}}$$

wherein a and b are the ratios of a compound of formula I and the compound of formula II in the mixture resp., and the indexes (I), (II) and (I+II) refer to the compound of formula I, the compound of formula II and the a:b mixture of a compound of formula I and the compound of formula II. In the case of synergism EC (I+II)90 theor. is greater than ED(I+II)90 exp., or $$SF = \frac{EC(I + II)90\ theor.}{EC(I + II)90\ exp.} > 1$$

TEST RESULTS

The fungicidal activity obtained with oxadixyl (in aqueous spray liquid form of a 25% wettable powder formulation of Formulation Example 1 hereinafter)

dimethomorph (in aqueous spray liquid form of the 25% wettable powder formulation of Formulation Example 2 hereinafter)

oxadixyl+dimethomorph mixtures in weight ratio
1:1
1:2.5
1:6.25 against both the sensitive *Phytophthora infestans* strains 58 and the resistant *Phytophthora infestans* strains 13 is expressed in the following Tables I, II and III. The EC 90 exp. values for oxadixyl and dimethomorph specified in Tables I and II have been employed to calculate the EC 90 theor. values for the oxadixyl/dimethomorph mixtures expressed in Table III.

TABLE I

| *P. infestans* strain 58/Tomato | | | | | | |
|---|---|---|---|---|---|---|
| Concentration | % Control | | | | | EC 90 exp. |
| (ppm a.i.) | 500 | 125 | 31 | 8 | 2 | (in ppm) |
| Oxadixyl | 100 | 100 | 85 | 65 | 40 | 25 |
| Dimethomorph | 100 | 100 | 95 | 75 | 35 | 18 |
| Oxadixyl + dimethomorph | | | | | | |
| weight ratio 1:1 | 100 | 100 | 100 | 80 | 60 | 8.2 |
| 1:2.5 | 100 | 100 | 100 | 80 | 55 | 8.5 |
| 1:6.25 | 100 | 100 | 100 | 85 | 50 | 8.2 |

TABLE II

| Concentration | _P. infestans_ strain 13/Tomato | | | | | EC 90 exp. |
|---|---|---|---|---|---|---|
| | % Control | | | | | |
| (ppm a.i.) | 500 | 125 | 31 | 8 | 2 | (in ppm) |
| Oxadixyl | 60 | 45 | 30 | 20 | 5 | 8548 |
| Dimethomorph | 100 | 100 | 90 | 70 | 40 | 22 |
| Oxadixyl + Dimethomorph | | | | | | |
| weight ratio 1:1 | 100 | 100 | 95 | 75 | 40 | 18 |
| 1:2.5 | 100 | 100 | 100 | 85 | 40 | 8.8 |
| 1:6.25 | 100 | 100 | 100 | 85 | 50 | 8.2 |

TABLE III

| | Factor of synergism (according to Wadley) | | | |
|---|---|---|---|---|
| Test Compound | Weight ratio | EC 90 exp | EC 90 theor | SF |
| (a) _P. infestans_ strain 58/Tomato | | | | |
| Oxadixyl | | 25 | | |
| Dimethomorph | | 18 | | |
| Oxadixyl + Dimethomorph | | | | |
| | 1:1 | 8.2 | 20.93 | 2.6 |
| | 1:2.5 | 8.5 | 19.57 | 2.3 |
| | 1:6.25 | 8.2 | 18.72 | 2.3 |
| (b) _P. infestans_ strain 13/Tomato | | | | |
| Oxadixyl | | 8548 | | |
| Dimethomorph | | 22 | | |
| Oxadixyl + Dimethomorph | | | | |
| | 1:1 | 18 | 43.89 | 2.4 |
| | 1:2.5 | 8.8 | 30.77 | 3.5 |
| | 1:6.25 | 8.2 | 25.51 | 3.1 |

The test results given in Table III demonstrate a synergistic effect for mixtures of between oxadixyl:-dimethomorph in weight ratios in the range of from 1:1 to 6.25.

For the weight ratio oxadixyl:dimethomorph in the range of from 1:2.5 to 1:6.3 the SF against oxadixyl resistant strains is greater than against oxadixyl sensitive strains. This suggests that the development of resistance against oxadixyl will be depressed when employing oxadixyl:dimethomorph mixtures in the range of from 1:2.5 to 1:6.3.

FORMULATION EXAMPLE 1

25% Oxadixyl
3% sodium dodecylsulphate
5% sodium ligninsulphonate
5% silica gel
62% kaolin

FORMULATION EXAMPLE 2

25% Dimethomorph
3% sodium dodecylsulphate
5% sodium ligninsulphonate
5% silicagel
62% kaolin

FORMULATION EXAMPLE 3

7.1% Oxadixyl
17.9% Dimethomorph
5.0% silicagel
62.0% kaolin
5.0% sodium ligninsulphonate
3.0% sodium dodecylsulphate

FORMULATION EXAMPLE 4

3.4% Oxadixyl
21.6% Dimethomorph
5.0% silicagel
62.0% kaolin
5.0% sodium ligninsulphonate
3.0% sodium dodecylsulphae.

The wettable powders of formulation Examples 1 to 4 are obtained by mixing of the components, subsequent milling of the mixture in an appropriate mill allowing a sufficiently fine particle size (equal to or smaller than 20 micrometer) followed by mixing of the milled material.

I claim:

1. A method of combatting phytophogenic fungi which comprises applying to the plants
   (a) a compound of formula I

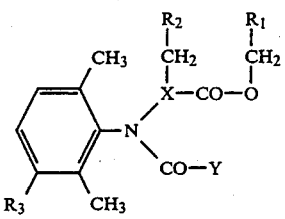

wherein
$R_1$ and $R_2$ together form a covalent bond,
$R_3$ is H,
X is N and
Y is $CH_2OCH_3$ in association with
(b) the compound of formula II

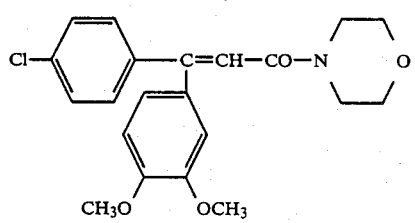

in a synergistic fungicidally effective aggregate amount wherein the weight ratio of the compound of formula I:the compound of formula II is in the range of from 1:1 to 1:6.5.

2. The method of claim 1 wherein the phytopathogenic fungi are of the class Oomycetes.

3. The method of claim 2, wherein the fungi are Phytophthora spp, Plasmopara spp, Pseudoperonospora spp or Peronospora spp.

4. The method of claim 3, wherein the plants are tomato, potato, grapevine, tobacco or cucurbit cultures.

5. The method of claims 1 to 4, wherein the aggregate amount of the compounds of formulae I and II lies in the range of from 500 to 1000 g per hectare of crop locus.

6. The method of claim 1, wherein the ratio lies in the range of from 1:2 to 1:6.3.

7. A fungicide composition comprising in a synergistic fungicidally effective aggregate amount:

(a) a compound of formula I

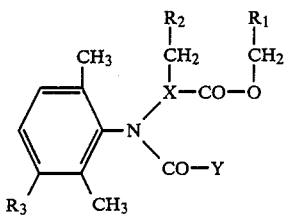

wherein
$R_1$ and $R_2$ together from a covalent bond, $R_3$ is H, X is N and
Y is $CH_2OCH_3$;

(b) the compound of formula II

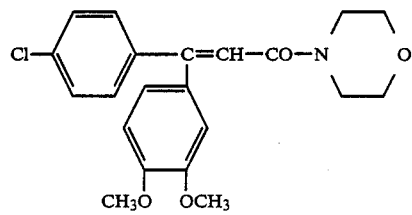

(c) and an inert agriculturally acceptable diluent wherein the weight ratio of the compound of formula I:the compound of formula II is in the range of from 1:1 to 1:6.5.

8. The fungicide composition of claim 7, wherein the weight ratio lies in the range of from 1:2.5 to 1:6.3.

* * * * *